United States Patent
Vignon et al.

(10) Patent No.: US 10,548,563 B2
(45) Date of Patent: Feb. 4, 2020

(54) ACOUSTIC HIGHLIGHTING OF INTERVENTIONAL INSTRUMENTS

(71) Applicant: KONINKLIJKE PHILIPS N.V., Eindhoven (NL)

(72) Inventors: Francois Guy Gerard Marie Vignon, Croton on Hudson, NY (US); Ameet Kumar Jain, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 845 days.

(21) Appl. No.: 14/901,152

(22) PCT Filed: Jun. 27, 2014

(86) PCT No.: PCT/IB2014/062646
§ 371 (c)(1),
(2) Date: Dec. 28, 2015

(87) PCT Pub. No.: WO2014/207706
PCT Pub. Date: Dec. 31, 2014

(65) Prior Publication Data
US 2016/0135780 A1    May 19, 2016

Related U.S. Application Data

(60) Provisional application No. 61/840,506, filed on Jun. 28, 2013.

(51) Int. Cl.
*A61B 5/05*    (2006.01)
*A61B 8/08*    (2006.01)
*G06T 7/00*    (2017.01)

(52) U.S. Cl.
CPC .......... *A61B 8/0841* (2013.01); *A61B 8/5207* (2013.01); *G06T 7/0012* (2013.01);
(Continued)

(58) Field of Classification Search
None
See application file for complete search history.

(56) References Cited

U.S. PATENT DOCUMENTS

| 4,249,539 A | 2/1981 | Vilkomerson et al. |
| 5,158,088 A | 10/1992 | Nelson et al. |

(Continued)

FOREIGN PATENT DOCUMENTS

| JP | 1993007589 A | 1/1993 |
| WO | 9216148 A1 | 10/1992 |

(Continued)

OTHER PUBLICATIONS

Breyer, et al., "Ultrasonically Marked Catheter—A Method for Positive Echographic Catheter Position Identification", Medical and Biological Engineering and Computing, vol. 22, No. 3, May 1, 1984, pp. 268-271.

(Continued)

*Primary Examiner* — Joel F Brutus

(57) ABSTRACT

A system for highlighting an instrument in an image includes a probe (122) for transmitting and receiving ultrasonic energy and a marker device (120) configured to respond to a received ultrasonic signal and emit an ultrasonic signal after a delay. A medical instrument (102) includes the marker device. A control module (124) is stored in memory and configured to interpret the ultrasonic energy received from the probe and from the marker device at the probe to determine a three dimensional location of the medical instrument to highlight a position of the marker device in an image.

18 Claims, 6 Drawing Sheets

(52) U.S. Cl.
CPC ............ *G06T 2207/10132* (2013.01); *G06T 2207/30204* (2013.01)

(56) References Cited

U.S. PATENT DOCUMENTS

| | | | |
|---|---|---|---|
| 5,161,536 A | 11/1992 | Lyons | |
| 5,779,638 A | 7/1998 | Vesely et al. | |
| 5,921,930 A | 7/1999 | Uberle | |
| 2002/0087156 A1* | 7/2002 | Maguire | A61B 18/00 606/41 |
| 2007/0276232 A1* | 11/2007 | Towe | A61B 8/0833 600/437 |
| 2008/0281205 A1* | 11/2008 | Naghavi | A61B 8/12 600/458 |
| 2010/0022871 A1* | 1/2010 | De Beni | A61B 8/0833 600/424 |
| 2013/0041252 A1 | 2/2013 | Vignon et al. | |

FOREIGN PATENT DOCUMENTS

| | | |
|---|---|---|
| WO | 2005055849 A1 | 6/2005 |
| WO | 2005063125 A1 | 7/2005 |
| WO | 2009063360 A1 | 5/2009 |
| WO | 2011138698 A1 | 11/2011 |
| WO | 2013001424 A2 | 1/2013 |

OTHER PUBLICATIONS

Mung et al: "A Non-Disruptive Technology for Robust 3D Tool Tracking for Ultrasound-Guided Interventions"; MICCAI 2011, Part I, LNCS 6891, pp. 153-160, 2011.

Vilkomerson et al: "A System for Ultrasonic Beacon-Guidance of Catheters and Other Minimally-Invasive Medical Devices"; IEEE Transactions on Ultrasonics, Ferroelctrics, and Frequency Control, vol. 44, No. 2, Mar. 1997, pp. 496-504.

\* cited by examiner

ACOUSTIC HIGHLIGHTING OF INTERVENTIONAL INSTRUMENTS

CROSS-REFERENCE TO PRIOR APPLICATIONS

This application is the U.S. National Phase application under 35 U.S.C. § 371 of International Application No. PCT/IB2014/062646, filed on Jun. 27, 2014, which claims the benefit of U.S. Provisional Patent Application No. 61/840,506, filed on Jun. 28, 2013. These applications are hereby incorporated by reference herein.

BACKGROUND

1. Technical Field

This disclosure relates to medical instruments and more particularly to a system and method for highlighting instruments using acoustics.

2. Description of the Related Art

Needles, catheters and other interventional tools are often difficult to visualize under ultrasound due to their specular nature and unfavorable incidence angles. One solution for marking a needle tip under ultrasound guidance is to embed a small ultrasound sensor at the tip of the needle. Such a sensor receives the direct ultrasound signals that impinge upon it as imaging beams from an ultrasound imaging probe sweep the field of view. Different ways of using these signals to highlight the position of the transducer in the ultrasound image have been proposed. These ways rely on time-of-flight of ultrasound from the imaging probe to the sensor for estimating the range coordinate of the sensor, and on the intensity of the received signals as the imaging beams sweep the field of view to recover the lateral coordinate. To estimate time of flight, one must have access to the line trigger events of the scanner, and to estimate the lateral coordinates, one must have access to the frame trigger event and to the coordinates and steering angles of the imaging beams.

SUMMARY

In accordance with the present principles, a system for highlighting an instrument in an image includes a probe for transmitting and receiving ultrasonic energy and a marker device configured to respond to a received ultrasonic signal and emit an ultrasonic signal after a delay. A medical instrument includes the marker device. A control module is stored in memory and configured to interpret the ultrasonic energy received from the probe and from the marker device at the probe to determine a three dimensional location of the medical instrument to highlight a position of the marker device in an image.

A method for determining a position of an instrument includes estimating a frame rate of an imaging probe; analyzing traces within a detection window to find a temporal maximum which best matches a position of a marker device mounted on an instrument to determine an arrival time; injecting an acoustic feedback signal into the imaging probe by emitting a delayed signal from the marker device to the imaging probe to simulate an echo back from the marker device mounted on the instrument; and displaying the echo in an image to identify the position of the instrument.

Another method for determining a position of an instrument, inserting an instrument inside an ultrasonic field of view; estimating a frame rate (T) of an imaging mode being employed; determining a temporal maximum ($t_0$) of received signals by a sensor mounted on the instrument with respect to an origin (o); switching the sensor to a transmit mode; emitting an impulse from the sensor at a time $t_1=t_0+nT$, n being an integer such that the impulse propagates toward an imaging probe and a subsequent signal is beamformed by a scanner machine; and displaying an echo coming from the sensor location in an image.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
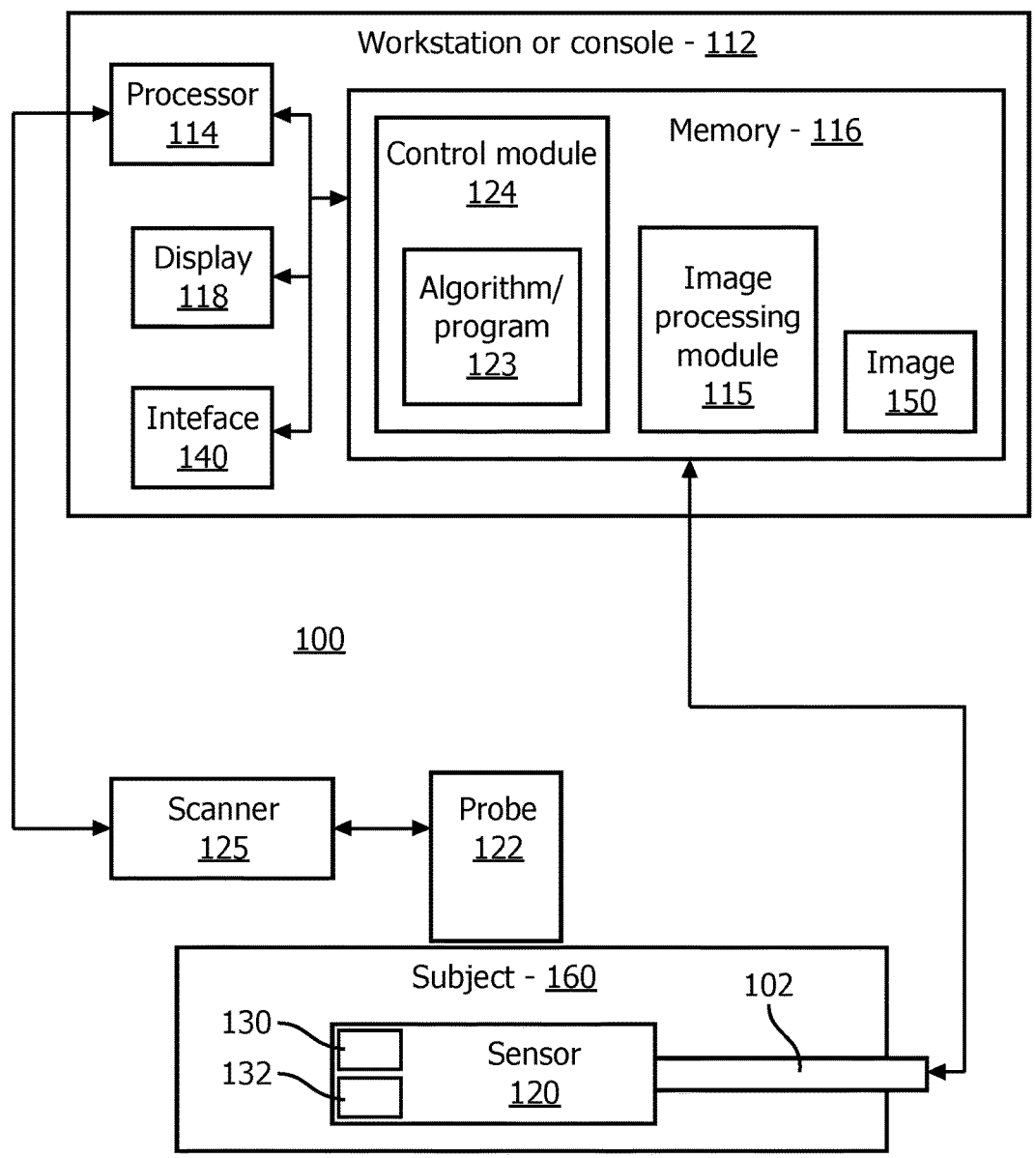
FIG. 1 is a block/flow diagram showing a system for highlighting an instrument in an image with ultrasound in accordance with one embodiment.

In accordance with the present principles, system and methods permit highlighting of a position of a sensor. A sensor or sensors are employed on a medical device (e.g., an interventional device) to 'inject' an acoustic signal at a right time inside an ultrasound (US) image. This injected acoustic signal will be perceived by the scanner as a response to its own acoustic field. The signal is processed by a scanner's beamforming pipeline and ultimately, visualized on the US image. Note that even though we may not know the time when the acoustic waves were transmitted by the scanner, they will nevertheless create a signal on the sensor, which is exploited for highlighting the sensor. When the device is inserted inside the US region, a one-time calibration step is run to estimate a frame rate (T) of the imaging mode being used. Second, a temporal maximum ($t_0$) of the signals received by the sensor is found, with respect to an arbitrary origin. Third, the sensor is switched to a transmit mode, and an impulse is emitted from it at a time $t_1=t_0+nT$, n being an integer. That impulse propagates toward an imaging probe and a subsequent signal is beamformed by the scanner machine. A final visual display shows an echo coming from the sensor location.

The present principles permit less reliance on the availability of particular scanner data for pinpointing the position of an instrument. For example, a frame, line triggers and beamforming parameters are no longer needed from the scanner. This allows ultrasound-equipped tools to be self-contained (no need for low-level interfacing with the scanner) thus allowing them to be usable with a broad installed base of ultrasound machines from any vendor. In one embodiment, the system is capable of on-the-fly reverse-engineering of crucial parameters from the imaging scanner, e.g., frame rate and line trigger positions, analog acoustic signal injection into the scanner's receive signal path, etc.

It should be understood that the present invention will be described in terms of needles; however, the teachings of the present invention are much broader and are applicable to any medical instruments or other instruments tracked by acoustic energy. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, etc. The elements depicted in the FIGS. may be implemented in various combinations of hardware and software and provide functions which may be combined in a single element or multiple elements. The present embodiments may be employed any time an instrument is inserted into the body under ultrasound guidance, this includes needle procedures (biopsies, ablation, anesthesia, pain management, abscess drainage, etc.), catheter procedures (heart repair, electrophysiology, etc.) or any other procedures.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Referring now to the drawings in which like numerals represent the same or similar elements and initially to FIG. 1, a system 100 is illustratively shown in accordance with one embodiment. System 100 may include a workstation or console 112 from which a procedure is supervised and/or managed. Workstation 112 preferably includes one or more processors 114 and memory 116 for storing programs and applications. Memory 116 may store an image processing module 115 configured to process signals from an ultrasonic scanner 125. Module 115 is configured to use the US signals to reconstruct structures deformations, deflections and other changes associated with a medical device, instrument or tool 102 and/or its surrounding region. The medical instrument 102 may include a needle, a catheter, a guidewire, a probe, an endoscope, a robot, an electrode, a filter device, a balloon device, or other medical component, etc.

An acoustic sensor (including a transmitter or transponder) 120 is mounted on the medical instrument 102 to be highlighted. A probe 122, such as a US probe 122 is provided for scanning a patient or subject 160. The probe 122 is capable of reception (to sense signal emission by the probe 122). The received signals at the probe 122 are coupled to a simple data-analysis and control module 124 stored in memory 116 and capable of some amount of signal processing in algorithm/program 123 (e.g., Fast Fourier Transform (FFT), max identification, optional curve fitting, etc.).

In particularly useful embodiments, the ultrasound sensor 120 is placed at the tip of a needle (for example). That sensor 120 senses ultrasound signals as beams from the imaging probe 122 as it sweeps the field of view. The US signals are analyzed by the workstation 112 and/or in the control module 124 to extract a frame repetition period T, and a time of arrival $t_0$ of a maximum signal at the sensor 120. One or more frames later, the sensor 120 is switched into a transmit mode and emits a pulse (at, e.g., $t_0+T$ or $t_0+nT$, where n is an integer). The scanner 125 interprets the pulse as being a high echo coming from a position of the sensor 120, thus highlighting the sensor 120 and, in turn, the instrument 102 on an image 150 even under slight out-of-plane alignment.

In particularly useful embodiments, the ultrasound sensor or marker device 120 includes a receive function 130 and a transmit function 132. The ultrasound sensor 120 may include a receiver/transmitter pair, a transponder or a transducer with a transmitter/receiver (T/R) switch on the interventional tool or instrument 102 to be highlighted. A transponder is a device that emits an identifying signal in response to an interrogating received signal. The signal received at the receiver function 130 of the sensor 120, while the imaging probe 122 emits ultrasound into the medium, is coupled to the data-analysis control module 124 capable of signal processing (FFT, max identification, optionally curve fitting) and slow switches. The transmit function 132 is provided for acoustic signal injection back into the medium (to the probe 122 to be processed in the control module 124).

In one example, the sensor 120 aboard the tool 102 includes a transponder (which is also used in a transmit mode). This may call for higher voltage circuits (in the tens of volts) and need to reasonably match the frequencies of the imaging probe 122 and that of the transponder (the signal from the transponder need not be filtered out in the scanner's receive signal path). The transponder may also include a (slow) T/R switch to switch between a receive mode and transmit mode. In another example, an additional ultrasound emitter for the transmit function 132 may be placed on the device close to the receiver function 130 (or co-located as a transceiver so that received and transmitted signals have a common location). This eliminates the need for a T/R switch and simplifies the detection/injection software.

A display 118 shows a location of the sensor location. Display 118 may also permit a user to interact with the workstation 112 and its components and functions, or any other element within the system 100. This is further facilitated by an interface 140 which may include a keyboard, mouse, a joystick, a haptic device, or any other peripheral or control to permit user feedback from and interaction with the workstation 112.

In another embodiment, a video signal-out from the scanner 125 and the instrument 102 with the sensor 120 are employed to compute a 3D location of the instrument 102 at any given time. The video-out signal is easily available on commercial scanners and is streamed into the computational workstation 112.

Figure 2:
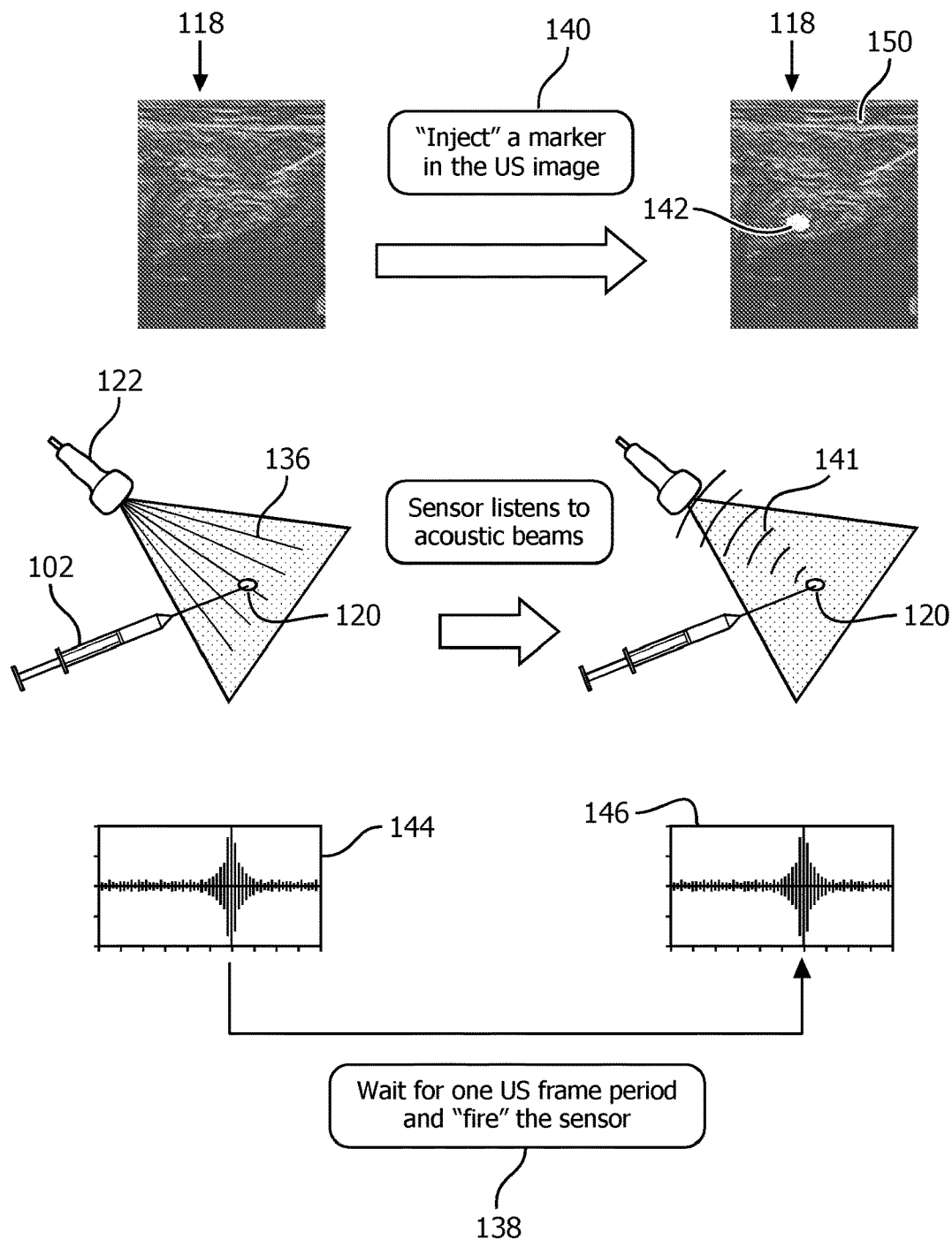
FIG. 2 is a conceptual diagram showing a system for highlighting the instrument with ultrasound in accordance with one embodiment.

Referring to FIG. 2, a conceptual diagram shows interaction between components in accordance with one illustrative embodiment. Signal injection is performed with the sensor 120 with a timed or responsive US emission. The sensor 120 is placed at the tip of the device 102 to be highlighted. Example signals 136 received by that sensor/transponder 120 during one imaging frame from the probe 122 are shown. The sensor 120 senses ultrasound signals 136 as beams from the imaging probe 122 sweep. This signal 136 is analyzed to extract the frame repetition period T, and the time of arrival $t_0$ of the maximum signal at the sensor 120. One or two (or more) frames later (138), the sensor 120 is switched into transmit mode and emits a pulse (at, e.g., $t_0+T$ or $t_0+2T$). The scanner 125 interprets the pulse as being a high echo coming from the position of the sensor 120, thus highlighting it on an image 150.

The system 100 identifies the position of the maximum and its timing relative to the line trigger information in plots 144 and 146. One (or more) frame period(s) 138 later, a signal 141 is injected by the sensor/transponder 120 back to the probe 122 with the appropriate timing to generate a bright marker 142 where the sensor 120 is located and is visible on the display 118.

Figure 3:
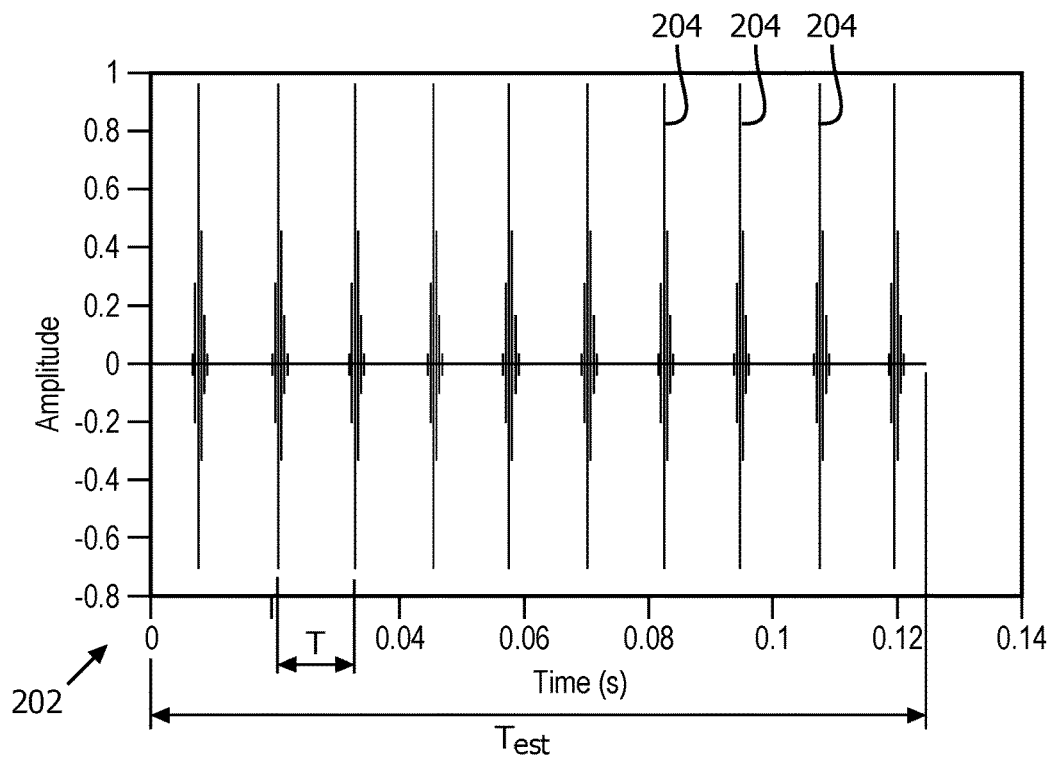
FIG. 3 is a plot of amplitude versus time showing ultrasound pulses for estimating frame rate in accordance with one embodiment.

Referring to FIG. 3, a frame rate T of the imaging probe needs to be estimated. This is done by listening to a received signal for a relatively long time $T_{est}$ (e.g., a quarter of a second, to record, e.g., 10 frames at 40 Hz) and analyzing the signal for its dominant period, i.e., by Fourier analysis. A received trace 202 is depicted in FIG. 3. On the trace 202, individual impulses 204 correspond to different beams hitting the sensor (120 on the device 102) (the amplitude varies as beams get closer and then farther from the sensor 120). The pattern is then repeated several times as several identical frames are acquired in continuous sequence. The trace 202 received by the sensor (120) during a time $T_{est}$ can be used to estimate the frame rate T of the system. Once this is done, the receiver system analyzes traces of a length $T_{detect}$ ($T<T_{detect}<2T$, ideally).

Figure 4:
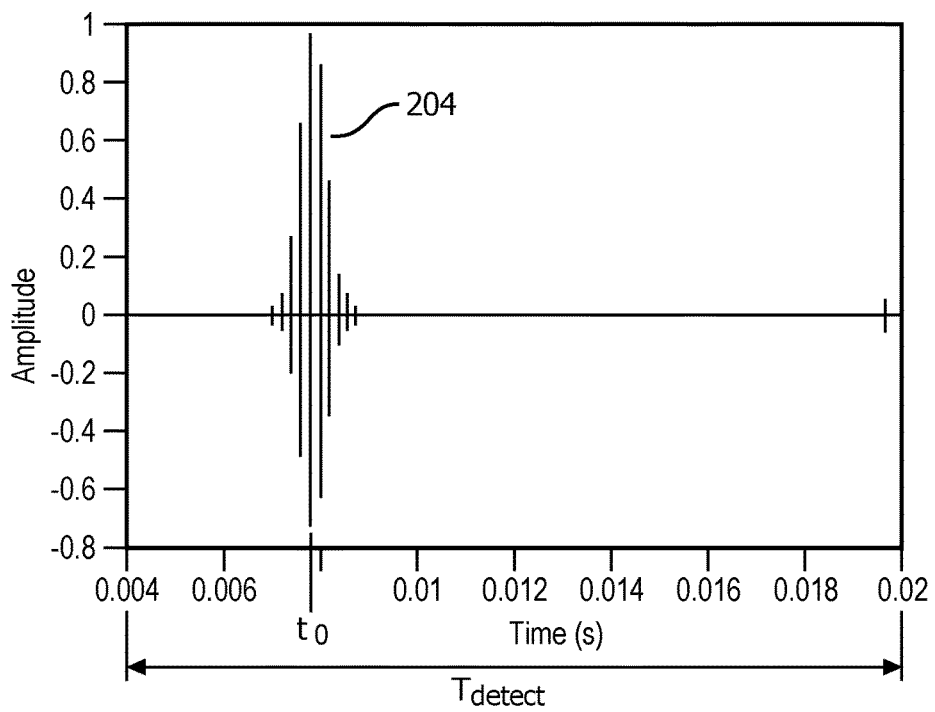
FIG. 4 is a plot of amplitude versus time showing an ultrasound pulse for determining a detection time in accordance with one embodiment.

Referring to FIG. 4, one of these traces 204 of a length $T_{detect}$ is depicted. Note that acquisition of these traces 204 is not synchronized with the frames. The system searches for the temporal maximum $t_0$ of this trace. That maximum corresponds to the instant when the pulse from the transmit event that is best aligned with the sensor 120 reaches the sensor 120. The trace received by the sensor 120 during a time $T_{detect}$ (e.g., $T_{detect}=1.2T$ here) is used to find the time $t_0$ when the most on-axis transmit reaches the sensor 120. $t_0$ is simply the temporal maximum of the trace 204.

Instead of a simple peak detection for identifying the beam closest to the sensor 120 and the arrival time, it may be advantageous to fit the curve or trace 204 (e.g., signals received by the sensor 120 during $T_{est}$) and fit the curve 204 to the local maxima of the individual pulses to a simple signal model, e.g., a Gaussian.

Next, an acoustic signal is injected back into the imaging probe 122 to create an echo that comes from the sensor position. It may also be desirable for the injected acoustic signal to blink (short periods of "injection on" alternating with periods of "injection off"). The human eye is more sensitive to a blinking signal. In other embodiments, visual effects may be imparted to the acoustic echo to change its size, change its shape or change its visual attributes. These visual effects may be introduced through the signal generated or sent back from the sensor 120. If the videostream is captured and synchronized to the signal acquisition and injection setup, differential images can be generated to highlight the injected signal (the "blink off" image is subtracted from the "blink on" image). The differential images can be enhanced and superimposed on the original image in an entirely image-processing chain that only requires access to video data from the scanner 125.

Figure 5:
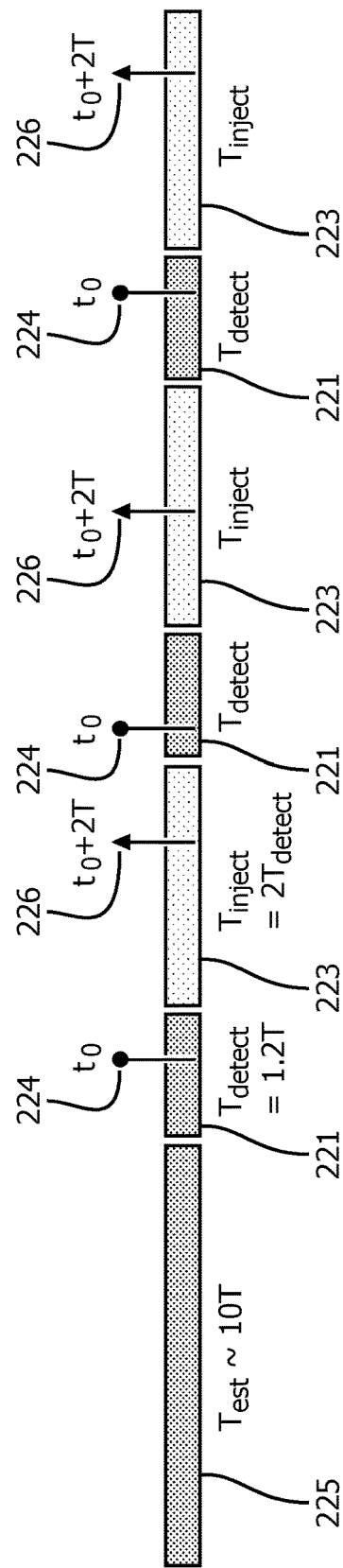
FIG. 5 is an event time line showing events occurring between a marker device of an instrument or tool and a probe in accordance with one embodiment.

For FIG. 5, two embodiments are illustratively described: the sensor 120 is a transponder (can be switched into a transmit mode with a slow T/R switch), or two transducers in close proximity are used, one being a receiver for signal detection and the other one being a transmitter for signal injection. Either way, the sequence of events outlined in FIG. 5 applies.

Referring to FIG. 5, a sequence of events for frame rate estimation, peak pulse detection, and pulse injection in the transponder embodiment are illustratively shown. Note that the external system's clock may be totally independent from the US scanner's clock. A relatively long period 225 ($T_{est}$) (long enough to comfortably span tens of frames) is used to estimate the imaging system's frame rate. Then, peak detection periods 221 (receive mode, darker shade) alternate with signal injection periods 223 (transmit mode, lighter shade). If a signal peak is detected at a time $t_0$, a signal is injected at $t_0+2T$; this creates an artificial echo at the position of the transponder two frames after its detection. Detection events 224 are depicted as rounded ends, and injection events 226 are arrows.

After detection, an impulse is sent from the transponder or transmitter at a time $t_0+nT$, n being an integer, preferably n=1 (transmitter embodiment) or 2 (transponder embodiment). This has the effect of creating an artificial echo that seems to come from the sensor position, n frames after the detection frame. The trace analysis and injection of a feedback signal may be repeated to actualize the position of the sensor 120. Frame rate estimation may also be repeated periodically to account for possible parameter changes as the user changes the imaging settings (imaging mode, settings, and depth may all affect frame rate).

Figure 6:
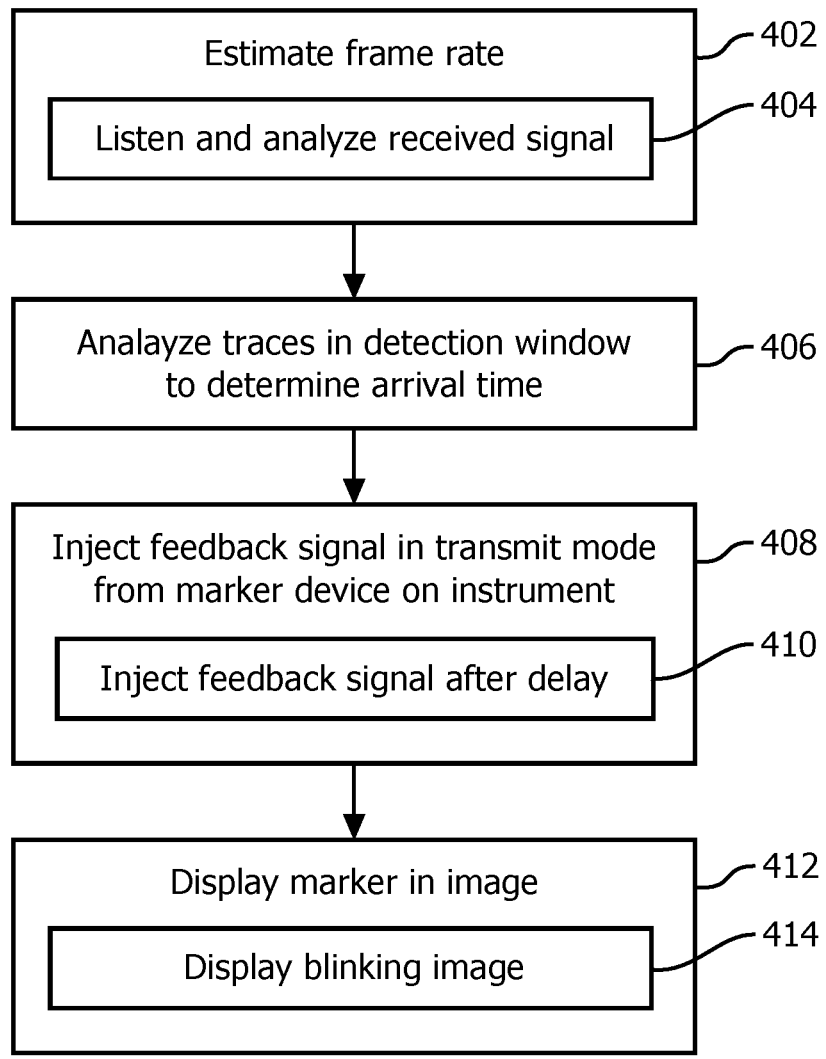
FIG. 6 is a flow diagram showing a method for tracking an instrument with ultrasound in accordance with one illustrative embodiment.

Referring to FIG. 6, a method for highlighting a position of an instrument is shown in accordance with one embodiment. In block 402, a frame rate of an imaging probe is estimated. In block 404, estimating the frame rate may include listening to a received signal for a period of time, and analyzing the received signal to determine its dominant period.

In block 406, traces are analyzed to determine if they are within a detection window to find a temporal maximum which best matches a position of a sensor or marker device mounted on an instrument to determine an arrival time. The detection window includes a detection time $T_{detect}$ between T and 2T, where T is the frame rate.

In block 408, an acoustic feedback signal is injected into the imaging probe using a transponder or transceiver (transmitter) on the imaging probe to simulate an echo back from the sensor mounted on the instrument. In block 410, the acoustic feedback signal is injected one or two frames after receiving an initial pulse from the probe. The number of frames n may be greater than 1 or 2 as well. In one embodiment, n=1 when the sensor includes a transmitter and n=2 when the sensor includes a transponder.

In block 412, a marker is displayed in an image to identify the position of the instrument. In block 414, displaying the marker in an image may include causing the marker to blink in the image. Other image effects may also be employed. In some embodiments, visual effects may be imparted to the acoustic echo (simulated echo) to change its size, change its shape or change its visual attributes. For example shapes such as triangles, circles, ovals, lines, etc. may be displayed in the image. These visual effects may be introduced through the signal generated by the scanner (e.g., for transponder applications) or sent back or generated by the sensor (120).

Figure 7:
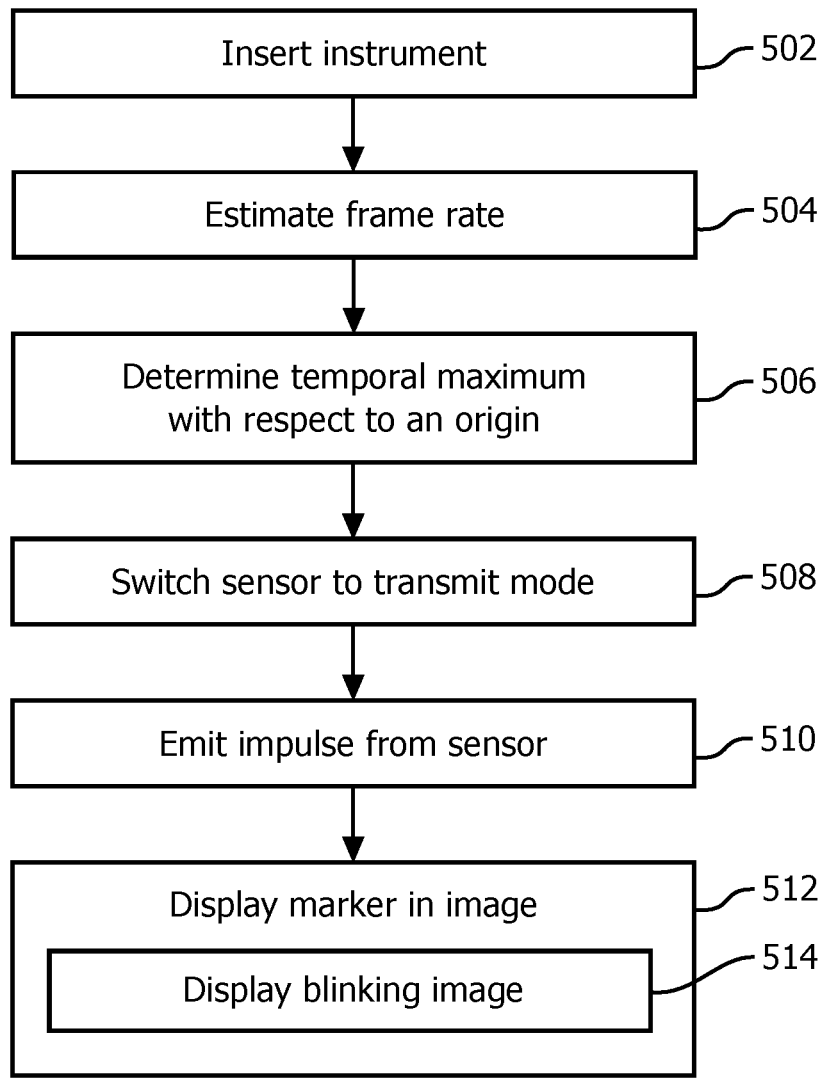
FIG. 7 is a flow diagram showing another method for tracking an instrument with ultrasound in accordance with illustrative embodiments.

Referring to FIG. 7, another method for highlighting a position of an instrument is shown in accordance with one embodiment. In block 502, an instrument is inserted inside an ultrasonic field of view. In block 504, a frame rate (T) of an imaging mode being employed is estimated. In block 506, a temporal maximum ($t_0$) of received signals is determined by a sensor or marker device mounted on the instrument with respect to an origin. In block 508, the sensor is switched to a transmit mode. In block 510, an impulse is emitted from the sensor at a time $t_1=t_0+nT$, n being an integer such that the impulse propagates toward an imaging probe and a subsequent signal is beamformed by a scanner machine. The number of frames n may be greater than 1 or 2 as well. In one embodiment, n=1 when the sensor includes a transmitter and n=2 when the sensor includes a transponder. In block 512, an echo coming from the sensor location is displayed in an image. In block 514, the echo is displayed in the image is caused to blink in the image. Other image effects may also be employed, as described above.

In interpreting the appended claims, it should be understood that:

a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for acoustic highlighting of interventional instruments (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A system for highlighting an instrument in an image, the system comprising:
    a marker device included on the instrument and configured to respond to a received ultrasonic signal received from a probe and to emit an emitted ultrasonic signal after a delay, the emitted ultrasonic signal to be received by the probe, wherein the probe is configured for transmitting and receiving ultrasonic signals to and from a volume, and the instrument is disposed in the volume, and wherein the emitted ultrasonic signal is injected to the probe at $t_0+nT$, where $t_0$ is a temporal maximum of the ultrasonic signals received by the marker device, T is frame rate, and n is an integer; and
    a controller configured to interpret the emitted ultrasonic signal received by the probe to highlight a position of the marker device in an image.

2. The system as recited in claim 1, wherein the marker device includes a transponder and the transponder includes a switch to change from a receive mode to a transmit mode.

3. The system as recited in claim 1, wherein the marker device includes a transceiver having a receiver and a transmitter.

4. The system as recited in claim 1, wherein n=1 when the marker device includes a transmitter.

5. The system as recited in claim 1, wherein n=2 when the marker device includes a transponder.

6. The system as recited in claim 1, wherein the controller is further configured to cause a display configured to display images collected using the probe to include in the images a bright area based on the emitted ultrasound signal received by the probe from the marker device.

7. A method for determining a position of an instrument inserted in a volume of an imaging probe, the method comprising:
    estimating a frame rate of the imaging probe;
    analyzing traces within a detection window to find a temporal maximum which best matches a position of a marker device mounted on the instrument to determine an arrival time, wherein the detection window includes a detection time $T_{detect}$ between T and 2T, where T is the frame rate;
    injecting an acoustic feedback signal into the imaging probe by emitting a delayed signal from the marker device to the imaging probe to generate a simulated echo back from the marker device mounted on the instrument; and
    displaying the simulated echo in an image to identify the position of the instrument.

8. The method as recited in claim 7, wherein estimating the frame rate includes listening to a received signal from the imaging probe for a period of time, and analyzing the received signal to determine its dominant period.

9. The method as recited in claim 7, wherein the acoustic feedback signal is injected at $t_0+nT$, where $t_0$ is a temporal maximum of signals received by the sensor, T is frame rate and n is an integer.

10. The method as recited in claim 9, wherein n=1 when the marker device includes a transmitter.

11. The method as recited in claim 9, wherein n=2 when the marker device includes a transponder.

12. The method as recited in claim 7, wherein displaying the simulated echo in an image includes causing the simulated echo to blink in the image.

13. The method as recited in claim 7, wherein displaying the simulated echo in an image includes changing a visual attribute of the simulated echo displayed in the image.

14. A method for determining a position of an instrument, the method comprising:
- inserting the instrument inside an ultrasonic field of view of an imaging probe;
- estimating a frame rate (T) of an imaging mode being employed;
- determining a temporal maximum ($t_0$) of signals from the imaging probe received by a sensor mounted on the instrument with respect to an origin (o);
- switching the sensor to a transmit mode;
- emitting an impulse from the sensor at a time $t_1=t_0+nT$, n being an integer, such that the impulse propagates toward the imaging probe to simulate an echo from the sensor mounted on the instrument, and a subsequent signal is beamformed by a scanner; and
- displaying the echo from a location of the sensor in an image.

15. The method as recited in claim 14, wherein n=1 when the sensor includes a transmitter.

16. The method as recited in claim 14, wherein n=2 when the sensor includes a transponder.

17. The method as recited in claim 14, wherein displaying the echo in the image includes causing the echo to blink in the image.

18. The method as recited in claim 14, wherein displaying the echo in the image includes changing a visual attribute of the echo displayed in the image.

* * * * *